United States Patent [19]
Scott et al.

[11] Patent Number: 5,712,387
[45] Date of Patent: Jan. 27, 1998

[54] HIGH YIELD STEREOSPECIFIC MANNOSYLATION

[75] Inventors: Ian L. Scott, Houston; Timothy P. Kogan, Sugarland, both of Tex.; Harold Meckler, Delmar, N.Y.

[73] Assignee: Texas Biotechnology Corporation, Houston, Tex.

[21] Appl. No.: 650,653

[22] Filed: May 20, 1996

[51] Int. Cl.$^6$ ............................ C07H 113/02; C07H 1/00
[52] U.S. Cl. ............................ 536/119; 536/115; 536/124
[58] Field of Search ................................... 536/119, 115, 536/124

[56] References Cited

PUBLICATIONS

Nouv. J. Chim., 10(3), 143–4, 1986.
Indian J. Chem., 11(7), 704–5, 1973.
Carbohydrate Research, 142, (1985), pp. 333–337.
Indian Journal of Chemistry, vol. 30B, May 1991, pp. 519–521.
Chemical Abstracts, vol. 80, No. 15, Apr. 1974, abstract No. 83439a.
Journal of the Chemical Society Perkin Transactions 1(4), 1079–82, 1990.
Synthesis (11), 883–5, 1981.

*Primary Examiner*—John Kight
*Assistant Examiner*—Everett White
*Attorney, Agent, or Firm*—Dressler, Rockey, Milnamow & Katz, Ltd.

[57] ABSTRACT

A process of preparing mannosylated alcohols or phenols in high chemical yield and purity using tetra-$\underline{O}$-pivaloylmannosylfluoride and a Lewis acid catalyst.

4 Claims, No Drawings

5,712,387

HIGH YIELD STEREOSPECIFIC MANNOSYLATION

TECHNICAL FIELD

This invention relates to the preparation of compounds containing mannose residues linked as the alpha-anomer with high stereospecificity, suitable for use as pharmaceutical agents where high purity and lack of contamination with the beta-anomer are important.

BACKGROUND OF THE INVENTION

At present, the treatments available for inflammatory disorders are limited and often non-specific, such as steroids or cytotoxic agents such as methotrexate. The vascular endothelium is the entry point for immune cells to tissues, therefore drugs which can block the interactions of these leukocytes and the endothelium may prevent leukocyte recruitment and ameliorate inappropriate inflammatory responses. Though a normal inflammatory response can be lifesaving in some situations the inflammatory response can be life-threatening as in the case of adult respiratory distress syndrome.

The inflammatory response depends upon activation of endothelial cells which then express molecules that initiate leukocyte rolling (selectins), firm adhesion (VCAM), and transmigration (PECAM). Selectins are divided into three types: E-selectin, an endothelial derived protein expressed early (4–6 hours) and falls towards baseline by 24–48 hours. E-selectin supports adhesion of neutrophils, monocytes, eosinophils, and some lymphocytes. P-selectin is constitutively synthesized and stored in platelets and endothelial cells. P-selectin is expressed very early and reaches peak levels within 2 hours and falls to baseline within 4 hours. P-selectin supports adhesion of neutrophils, monocytes, and some lymphocytes. L-selectin is constitutively expressed by leukocytes and supports the adhesion of neutrophils, eosinophils and monocytes. All three selectins bind the tetrasaccharide sialyl Lewis x (sLe$^x$).

Recently, a series of designed small molecule mimetics of sLe$^x$ which inhibit E-, P-, and L-selectin, and show efficacy in animal models of inflammatory disease have been disclosed [U.S. Pat. No. 5,444,050; T. P. Kogan, B. Dupré, K. M. Keller, I. L. Scott, H. Bui, R. V. Market, P. J. Beck, J. A. Voytus, B. M. Revelle and D. Scott, *J. Med. Chem.* 1995, 38, 4976–4984 ]. In each case these compounds contain mannose residues in the alpha configuration which are important for their efficacy as selectin antagonists. Clearly it is critical that methodology be available for the synthesis of these compounds in high yield and with high stereochemical integrity.

Published methodology for the mannosylation includes treatment of an alcohol or phenol with mannose pentaacetate in the presence of a Lewis acid catalyst. [J. Dahmén, T. Frejd, G. Magnusson, G. Noori, *Carbohydr. Res.*, 1983, 114, 328] Such glycosylation conditions typically lead to difficulties in driving the reaction to completion, and frequently result in contamination with 1 to 3% of the beta anomer and ortho ester by-products, which can be very difficult to remove by purification.

SUMMARY OF THE INVENTION

The present invention provides a process for alpha-mannopyranosylation of alcohols and phenols in both high chemical yield, and with high stereospecificity to give the alpha anomer as shown below.

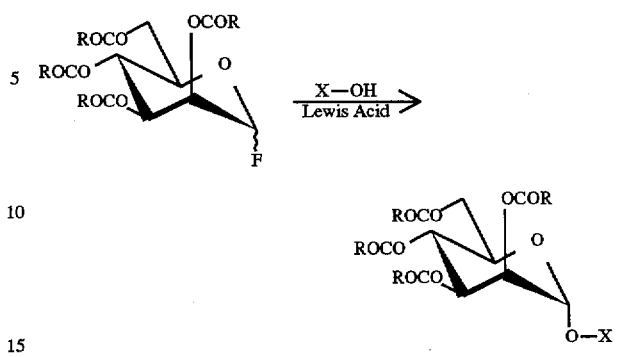

where X is alkyl or aryl, R is lower alkyl, branched alkyl, aryl, aralkyl or OG; where G=lower alkyl, branched alkyl, aryl or aralkyl.

A process of the present invention begins with an alcohol or phenol (X-OH) along with a protected mannosyl fluoride. The alcohol or phenol is treated with the protected mannosyl fluoride in the presence of a Lewis acid to give the alpha-mannosylated product.

More specifically, where R is an methyl, ethoxy, benzyl, isobutyryl, or tert-butyl protecting group [R=—CH$_3$, —OEt, —CH$_2$Ph, —CH(CH$_3$)$_2$, —C(CH$_3$)$_3$], mannosylation proceeds rapidly in high chemical yield, however the more bulky protecting groups (i.e. pivaloyl, other sterically hindered acyl groups) give higher degrees of alpha stereospecificity.

The present invention is also directed to novel compounds of the formula:

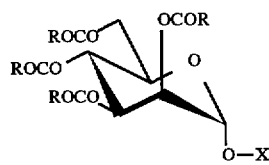

where X is alkyl or aryl, and R is lower alkyl, branched alkyl, aryl, aralkyl or OG, where G is lower alkyl, branched alkyl, aryl or aralkyl; compounds of the formula:

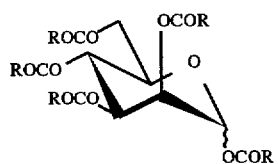

where R is as defined above; and compounds of the formula:

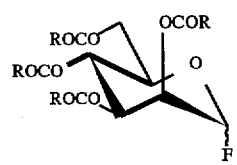

where R is as defined above, but may not be methyl.

DETAILED DESCRIPTION OF THE PREFERRED EMBODIMENTS

As used herein; the term "alkoxy" shall mean an alkyl group attached to a molecule through an oxygen atom including, but not limited to, methoxy, ethoxy, isopropoxy, n-butoxy, sec-butoxy, isobutoxy, tert-butoxy and the like; and the term "alkyl" shall mean a monovalent straight chain or branched chain group of 1 to 6 carbon atoms including, but not limited to, methyl, ethyl, n-propyl, isopropyl, n-butyl, sec-butyl, isobutyl, tert-butyl and the like. The term "aryl" refers to unsubstituted and substituted aromatic hydrocarbon radicals such as phenyl, naphthyl, biphenyl and the like. Preferred aryl radicals include

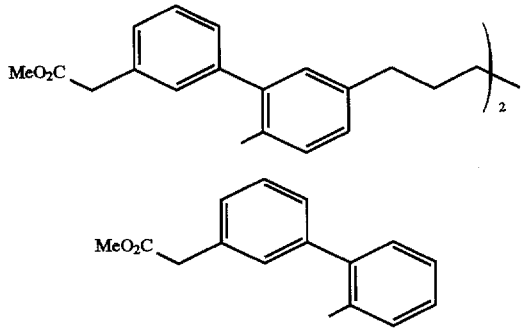

It has been found that glycosylation of alcohols or phenols using the known mannose pentaacetate/Lewis acid catalyzed procedure is subject to two problems. First, it is very difficult to drive this reaction to completion, even with the use of excess reagents, the reaction has a tendency to 'stall'. Secondly, the reaction leads to detectable quantities of the beta-anomer, along with ortho ester by-products, often in the 1 to 3% range. The combination of these observations makes this reaction of limited utility in the scale-up and manufacture of high purity chemicals and pharmaceutical agents that contain a mannose residue.

An alcohol or phenol is reacted with a mannosyl fluoride in the presence of a Lewis acid catalyst to give the glycoside. This reaction proceeds rapidly to completion in high chemical yield. The choice of protecting groups on the mannose residue is selected from any of the acyl [—O—C(=O)R] or carbonate based [—O—C(=O)OR] protecting groups. These are preferred over alkyl (e.g. benzyl), silyl, or acetonide based protection strategies since the presence of the carbonyl oxygen of the acyl or carbonate group at the 2-position enhances alpha-glycoside stereospecificity through participation with the incipient carbocation at the 1-position in the course of glycosylation.

Especially preferred are sterically bulky protecting groups, for example (but not limited to) isoproyloxy, pivaloyl, which help enhance stereospecificity in the process of glycosylation, and reduce the extent of ortho ester formation.

A preferred starting material for this process is mannose pentaacetate, which can be purchased (Sigma and other suppliers), or synthesized in high purity, without significant contamination with furanose sugars. However this invention is not intended to be limited to the use of mannose pentaacetate as a starting material, and those skilled in the art will be familiar with other potential mannose sources which can lead to mannosylfluoride and/or per-O-protected mannosylfluoride.

When mannose penta acetate is utilized as a starting material it is reacted with HF-pyridine to produce tetra-O-acetyl-α-D-mannopyranosyl fluoride which is dissolved in methanol and reacted with potassium carbonate to produce tetra-O-hydroxy-α-D-mannopyranosyl fluoride which is reacted with RCOCl, where R is as defined above to produce tetra-O-acyl-α-D-mannopyranosyl fluoride which is then reacted with an alcohol or phenol in the presence of a Lewis acid to produce the α-mannosylated product.

This method of practicing the present invention is illustrated below:

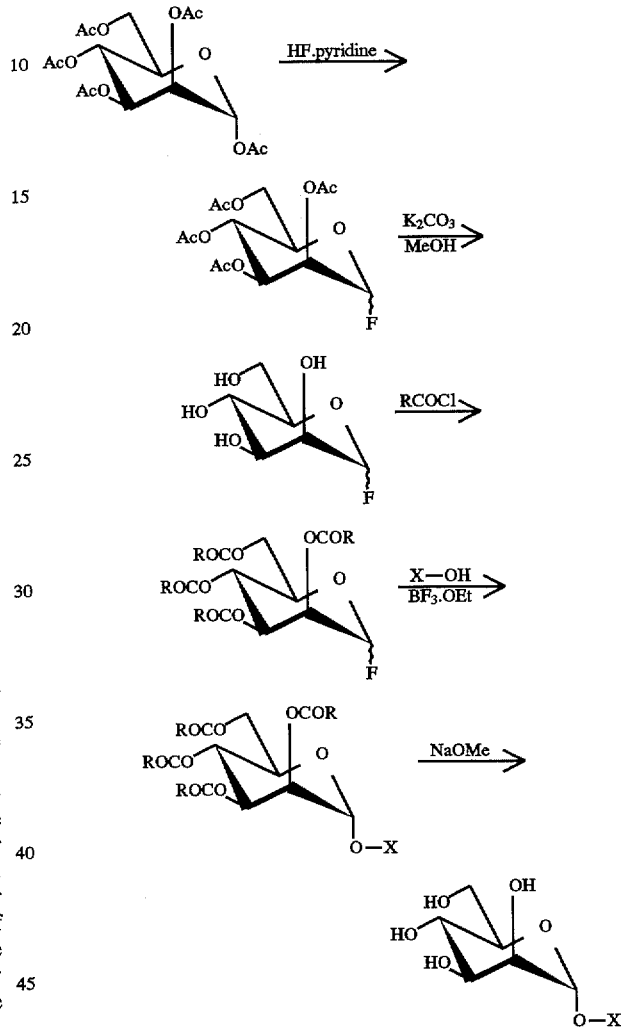

An alternate more preferred method of practicing the present invention in which the cheaper starting material, L-D-mannose, is illustrated below. In this method an acyl chloride is added to α-D-mannose to produce the corresponding penta-O-acyl-α-D-mannopyranoside which is then reacted with HF-pyridine, followed by reaction with an alcohol or phenol as described above to give the glycoside.

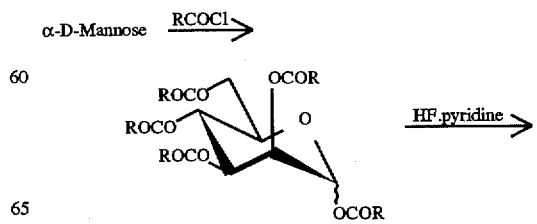

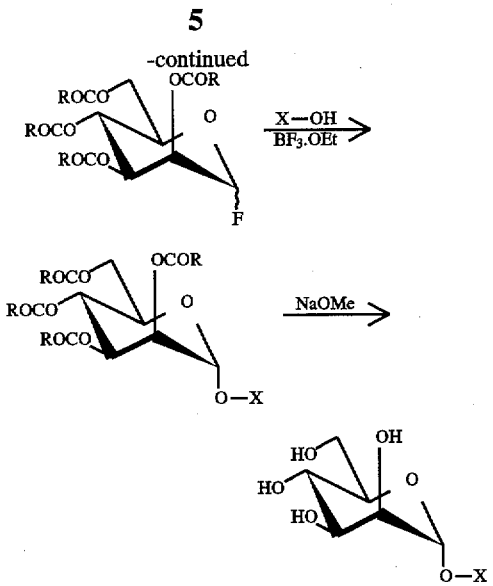

A further alternate method of practicing the present invention is illustrated below:

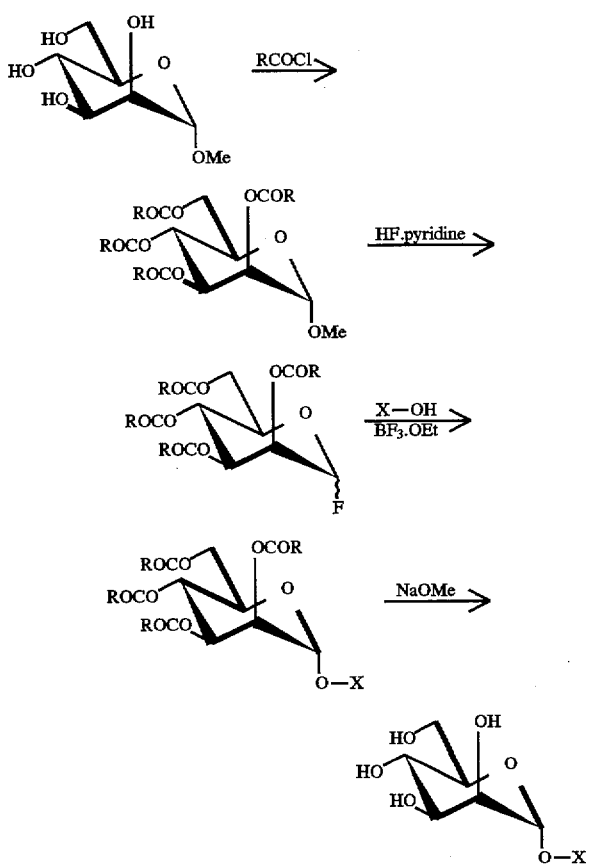

The invention is further illustrated by the following representative examples:

EXAMPLE 1

Tetra-O-Acetyl-α-D-mannopyranosyl fluoride

Mannose pentaacetate (100 g) was stirred with dichloromethane (10 mL) in a FEP Erlenmeyer. Cold HF-pyridine (100 g) was added and the resulting solution stirred at 40° C., sealed, overnight. The solution was poured into a FEP separating funnel containing water and chloroform and shaken. The chloroform layer was washed once with water and once with saturated sodium bicarbonate. The aqueous layers were neutralized with sodium hydroxide. The organic solution was dried over magnesium sulfate and concentrated under reduced pressure. The product was purified by plug chromatography (silica, eluent hexane/EtOAc). Yield 74.06 g, 80%.

Tetra-O-pivaloyl-α-D-mannopyranosyl fluoride

Step One

Tetra-O-acetyl-D-mannopyranosyl fluoride (74 g) was dissolved in methanol (1 L) and potassium carbonate (0.5 g) added. The mixture was stirred at room temperature until all the acetates were removed (TLC CHCl$_3$/MeOH (8:2) gave a baseline spot. The solvent was removed under reduced pressure at 40° C. The remaining methanol was removed by evaporation of a small volume of 1,2-dimethoxyethane (3×). The crude mannosyl fluoride was used immediately in the next step.

Step Two

The residue was stirred with pyridine (500 mL) and cooled to 0° C. Pivaloyl chloride (200 mL) was added dropwise, followed by 4-dimethylaminopyridine (3 g) and the mixture stirred at 0° C. for 30 minutes, room temperature for 30 minutes and then heated at 70° C. overnight. After cooling to 50° C., methanol (50 mL) was added slowly and the mixture stirred at for 1 hour at 50° C. before cooling to room temperature. The mixture was diluted with EtOAc and the solid removed by filtration and washed with EtOAc. The combined organic solutions were concentrated under reduced pressure using high vacuum to remove most of the pyridine. The residue was taken up in EtOAc and washed with water, hydrochloric acid (2M) (2×), water, sodium hydroxide (2M), water and saturated sodium chloride. The solution was dried over magnesium sulfate and concentrated under reduced pressure. Chromatography (silica, hexane/EtOAc) gave 87.48 g (80%).

1,6 Bis-[3-(3-carbomethoxymethylphenyl)-4-(tetra-O-pivaloyl-α-D-mannopyranosyl)oxyphenyl]hexane To an ice-cold solution of tetra-O-pivaloyl-α-D-mannopyranosyl fluoride (66.4 g) and bisphenol (1,6 Bis-[3-(3-carbomethoxymethylphenyl)-4-hydroxyphenyl]hexane, 25.4 g), in dichloromethane (430 mL) was added BF$_3$-OEt$_2$ (47.3 mL) dropwise and the ice-cold mixture stirred for 1 hour. The mixture was diluted with EtOAc and washed with water (2×), sodium hydroxide (2M), water and saturated sodium chloride, dried over magnesium sulfate and concentrated under reduced pressure. Purification by chromatography (silica, hexane/EtOAc ) gave 59.82 g, 89%.

1,6 Bis-[3-(3-carbomethoxymethylphenyl)-4-α-D-mannopyranosyl)oxyphenyl]hexane sodium alkoxide To a solution of the per-pivaloylglycoside ( 11.6 g) in THF (24 mL) was added methanol (24.4 mL) followed by an ice-cold solution of freshly prepared sodium methoxide in methanol (0.5 g of Na in 24.4 mL), and the mixture stirred at room temperature overnight. The precipitate was collected by filtration and washed with a small volume of THF/methanol (2:1) (2×) and acetone. The solid was purified further by stirring with acetone and filtering. Yield 6.29 g.

EXAMPLE 2

Penta-O-pivaloyl-α-D-mannopyranoside

To mannose (45 g), DMAP (3 g), chloroform (500 mL) and pyridine (500 mL) were added. After cooling to −5° C. pivaloyl chloride (193 mL) was added dropwise. When the addition was complete the mixture was stirred at room temperature for 30 minutes and then at 70° C. for 3 days. The mixture was cooled to 20° C. and methanol (50 mL) added dropwise. After stirring at room temperature for 4 hours the reaction was quenched into water (1.5 L) with vigorous stirring. The organic layer was washed with hydrochloric acid (2M) (2×1.5 L) and saturated sodium bicarbonate (1×2 L). After drying over sodium sulfate and Clarion 470 Bentonite clay the mixture was concentrated under reduced pressure, initially at 45° C. and then at 70° C. (to remove the methyl pivaloate). A small quantity was removed and was crystallized from methanol with scraping. The bulk material was decolourized by heating with Clarion 470 (5 g) in methanol at 65° C. After vacuum filtration to remove the clay, the solution was allowed to cool to room temperature and seeded. After standing overnight only a few crystals had formed. Stirring (mag. stirrer) gave a white slurry which was collected and dried at 40° C. Yield 77.7 g. A second crop was obtained from the mother liquors (23.1 g).

Tetra-O-pivaloyl-α-D-mannopyranosyl fluoride (from the above pentapivaloate)

An FEP (Nalgene Teflon Flip from Fisher scientific) Erlenmeyer was charged with mannose pentapivaloate (3.56 g) and dichloromethane (0.5 mL). Cold HF-pyridine (5 mL) was added and the resulting solution stirred at 40° C. overnight. The solution was poured into a HiP separating funnel, diluted with water and dichloromethane, and shaken. The organic layer was washed with water (2×), dilute sodium hydroxide, water and saturated sodium chloride. The organic solution was dried over magnesium sulfate and concentrated under reduced pressure. Crude yield 2.5 g. The product was purified by chromatography (silica, eluent hexane/EtOAc gradient 14:1). It can also be crystallized from methanol.

EXAMPLE 3

Tetra-O-pivaloyl-α-D-mannopyranosyl fluoride (from methyl 2,3,4,6-pentapivaloyl-α-D-mannopyranoside)

An FEP (Nalgene Teflon FEP from Fisher scientific) Erlenmeyer was charged with methyl 2,3,4,6-pentapivaloyl-α-D-mannopyranoside (8.8 g). Cold HF-pyridine (10 mL) was added and the resulting solution stirred at 40° C. for 7 d. The solution was poured into a FEP separating funnel, diluted with water and dichloromethane, and shaken. The organic layer was washed with water (2×), dilute sodium hydroxide, water and saturated sodium chloride. The organic solution was dried over magnesium sulfate and concentrated under reduced pressure. The product was purified by chromatography (silica, eluent hexane/EtOAc gradient 14:1). It can also be crystallized from methanol.

What is claimed is:

1. A process of preparing a compound of the formula:

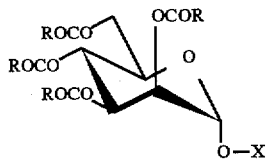

where X is alkyl or aryl and R is branched alkyl, aryl, aralkyl or OG where G is lower alkyl, branched alkyl, aryl or aralkyl, comprising reacting a mannosyl fluoride compound of the formula:

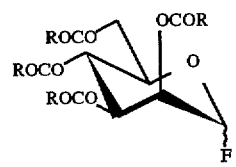

where R is as defined above, with a compound of the formula XOH in the presence of a Lewis acid where X is alkyl or aryl.

2. The process of claim 1 wherein the reaction is performed by reacting the mannosyl fluoride with an alcohol or phenol in the presence of boron trifluoride-etherate.

3. A process of preparing a compound of the formula:

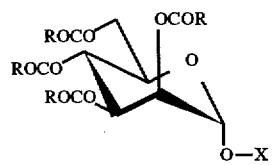

where R is lower alkyl, branched alkyl, aryl, aralkyl or OG, where G is lower alkyl, branched alkyl, aryl or aralkyl, and X is:

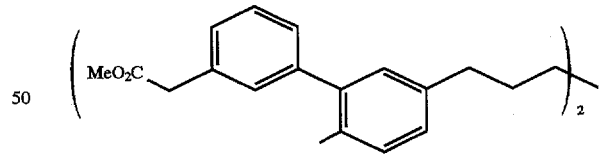

comprising reacting a compound of the formula:

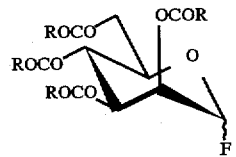

where R is as defined above with a compound of the formula XOH, where X is as defined above, in the presence of a Lewis acid.

4. A process of preparing a compound of the formula:
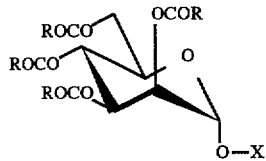
wherein R is lower alkyl, branched alkyl, aryl, aralkyl or OG, where G is lower alkyl, branched alkyl, aryl, or aralkyl, and X is:
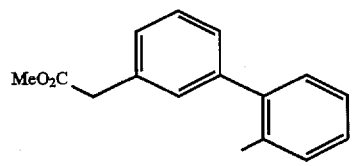
comprising reacting a compound of the formula:
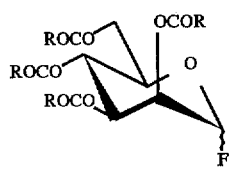
where R is as defined above, with a compound of the formula XOH, where X is as defined above in the presence of a Lewis acid.
* * * * *